(12) United States Patent
Migliaccio et al.

(10) Patent No.: US 10,646,523 B2
(45) Date of Patent: May 12, 2020

(54) COMBINATION COMPRISING SPIRULINA AND PALMITOYLETHANOLAMIDE AND/OR SALTS OR PHARMACEUTICALLY ACCEPTABLE DERIVATIVES THEREOF AND THEIR FORMULATIONS, FOR USE IN THE PREVENTION AND/OR IN THE TREATMENT OF HYPERACTIVATED TISSUE CONDITIONS

(71) Applicant: AGAIN LIFE ITALIA SRL, Schio (IT)

(72) Inventors: Raffaele Migliaccio, Monza (IT); Carmela Migliaccio, Monza (IT); Antonella Sardei, Molina di Malo (IT)

(73) Assignee: AGAIN LIFE ITALIA SRL, Schio Vicenza (IT)

( * ) Notice: Subject to any disclaimer, the term of this patent is extended or adjusted under 35 U.S.C. 154(b) by 0 days.

(21) Appl. No.: 15/519,611

(22) PCT Filed: Oct. 20, 2015

(86) PCT No.: PCT/IB2015/058074
§ 371 (c)(1),
(2) Date: Apr. 17, 2017

(87) PCT Pub. No.: WO2016/063217
PCT Pub. Date: Apr. 28, 2016

(65) Prior Publication Data
US 2017/0246227 A1 Aug. 31, 2017

(30) Foreign Application Priority Data
Oct. 22, 2014 (IT) .............. MI2014A1825

(51) Int. Cl.
| | |
|---|---|
| A61K 45/00 | (2006.01) |
| A61K 47/00 | (2006.01) |
| A01N 63/00 | (2020.01) |
| A01N 63/04 | (2006.01) |
| A01N 65/00 | (2009.01) |
| A61K 35/748 | (2015.01) |
| A61K 31/164 | (2006.01) |
| A61K 31/16 | (2006.01) |

(52) U.S. Cl.
CPC ............ *A61K 35/748* (2013.01); *A61K 31/16* (2013.01); *A61K 31/164* (2013.01)

(58) Field of Classification Search
CPC ..... A61K 39/39; A61K 49/0433; A01N 63/04
See application file for complete search history.

(56) References Cited

U.S. PATENT DOCUMENTS

| | | | | |
|---|---|---|---|---|
| 2002/0120242 A1* | 8/2002 | Tyrrell | ................ | A61F 13/8405 604/364 |
| 2004/0157932 A1* | 8/2004 | Saebo | ................. | A23K 20/105 514/625 |
| 2008/0193597 A1 | 8/2008 | Alleon | | |
| 2008/0260695 A1 | 10/2008 | Lu | | |
| 2012/0107300 A1 | 5/2012 | Schirripa | | |

FOREIGN PATENT DOCUMENTS

| | | |
|---|---|---|
| NL | 2011448 | 3/2014 |
| WO | WO 2013183907 | * 12/2013 |

OTHER PUBLICATIONS

Dr. Cath Recipe—Spirulina Green Devil's egg, Jul. 2012.*
Lorenz-Spirulina Pacifica Tech Bulletin #053, 1999.*
Zahriijian et al., J. Agr. Sci. Tech, 2013; 15: 1353-1360.*
Petrosino et al., British Journal of Pharmacology, 2017; 174: 1349-1365 (Year: 2017).*
Iimsam Artical, What the United Nations Says About Spirulina,, Dec. 2010.
Akao, Y. et al., Cancer Sci., vol. 100, No. 8, p. 1494-1501, 2009.
Coburn, A.F., et al., J. Exp. Med . . . vol. 100, No. 5, p. 425-435, 1954.
Gemma, C., et al., J. Neurosci, vol. 22, No. 14, p. 6114-6120, 2002.
Hernandez-Corona, A., et al., Antiviral Res., vol. 56, No. 3, p. 279-285, 2002.
International Searchr Report for PCT/IB2015/058074 dated Dec. 4, 2015.
Khan, M., et al., Am J Physiol Heart Circ Physiol., vol. 209, No. 5, p. H2135-45, EPUB, Dec. 22, 2005.

(Continued)

*Primary Examiner* — Gary B Nickol
*Assistant Examiner* — Lakia J Jackson-Tongue
(74) *Attorney, Agent, or Firm* — Hueschen and Sage

(57) ABSTRACT

The present invention relates to the combination of spirulina and palmitoylethanolamide (PEA) and/or pharmaceutically acceptable derivates or salts thereof, pharmaceutical formulations comprising the combination of spirulina and PEA and/or pharmaceutically acceptable derivates or salts thereof, optionally together with at least one physiologically acceptable excipient, and the use of the combination of spirulina and PEA and/or pharmaceutically acceptable derivates or salts thereof and formulations which include the said combination, for use in the prevention and/or treatment of tissue hyperactivation states, in the prevention and/or treatment of inflammatory pathologies, in the prevention and/or treatment of alterations in cardiac and/or coronary tissue, in the prevention and/or treatment of alterations in the vascular tissue, in the prevention and/or treatment of ophthalmic pathologies, preferably in the prevention and/or treatment of macular degeneration pathologies and glaucoma, in the prevention and/or treatment of dyslipidemia, in the prevention and/or treatment of alterations in pulmonary tissue, in the prevention and/or treatment of alterations in pelvic tissues, in the prevention and/or treatment of cellular alterations due to carcinogenesis, and/or in the prevention and/or treatment of dermatological alterations.

2 Claims, No Drawings

(56) References Cited

OTHER PUBLICATIONS

Kuehl, et al., Journal of American Chemical Society, vol. 79, No. 19, p. 5577-5578, Oct. 20, 1957.
Matias, I., et al., Biochim Biophys Acta, vol. 1781, No. 1-2, p. 52-60, 2007.
Nagaoka, S., et al., J. Nutr., vol. 135, No. 10, p. 2425-2430, 2005.
Samuels, R., et al., J Med Food, vol. 5, No. 2, p. 91-96, 2002.
Ueda, N., et al., J Biol Chem. vol. 276, No. 38, p. 35552-35557, EPUB 200, 2001.
Wang, Y., et al., Exp Neurol., vol. 193, No. 1, p. 75-84, 2005.
Written Opinion for PCT/IB2015/058074 Filed Oct. 20, 2015.

* cited by examiner

COMBINATION COMPRISING SPIRULINA AND PALMITOYLETHANOLAMIDE AND/OR SALTS OR PHARMACEUTICALLY ACCEPTABLE DERIVATIVES THEREOF AND THEIR FORMULATIONS, FOR USE IN THE PREVENTION AND/OR IN THE TREATMENT OF HYPERACTIVATED TISSUE CONDITIONS

PRIOR ART

Any body tissues, such as, for example, those of the brain, nervous system, skin, mucosa, blood, heart, lungs, etc., and—more specifically—any part thereof, represents a microenvironment which is able to perform the specific biological and physiological functions of the said tissue.

Tissues ensure their own defence against various types of damage (noxa), which may be of septic, traumatic, degenerative, etc. origin, whilst, in an effective and functional manner, they perform all the biological functions for which they are intended. The damage which tissues may suffer may also be due to alterations in the intercellular "messages", which may be the result of alterations of a hormonal, immune, etc. type. The said alterations in the communication between the cells of a tissue determine a response in the tissue microenvironment which may determine an altered tissue reaction, thereby triggering a series of reactions which trigger alterations.

It is well known within the art that all tissues "communicate" reciprocally and in an active manner, and therefore, the skin tissue, for example, communicates with the nervous, blood, etc. tissues. It is worthwhile underlining that every tissue microenvironment is part of the tissue to which such environment belongs and that the tissues constitute the organ of reference, with precise bio-physiological specifications, and that the organs constitute the apparatuses, etc. Obviously, any alteration in the apparatus has repercussions on the organ and, hence, on the tissues and therefore on the tissue microenvironment. It is therefore evident that any alteration in the microenvironment determines alterations in the organ and/or apparatus. For example, an alteration in the microenvironment of the intestinal villi alters the intestinal tissue and hence results in alterations in the digestive system.

Every tissue and, more specifically, every tiny part thereof (microenvironment) is able to carry out that which is required thereof by the body, but every tissue is also able to activate defence mechanisms against various forms of aggression and, at the same time, is able to repair damage suffered. This type of microtissue "behaviour" requires the tissue, and the component cells thereof, to be able to activate all the defence and repair systems able to restore the pre-noxa functions. Also during degeneration due to pathologies and/or noxa of a degenerative origin, the tissue activates all the necessary defence mechanisms and if the noxa is of a degenerative origin, the tissue carries out a series of reactions in order to limit the damage caused by the said degeneration.

These abilities, of the tissue microenvironment, make the tissue a sort of biological laboratory which can carry out a series of specific reactions. In the tissue, there are also immunocompetent system cells which are able to support the tissue against the various noxae which the tissue could suffer, thereby triggering a series of response reactions, the first of which is the inflammatory process.

As is known, the inflammatory response is an innate multifactoral physiological reaction characterised by the participation of different cells in the immune system, e.g. mast cells, macrophages, basophils and/or lymphocytes, with different intervention times. The first cell to intervene in the inflammatory process is the mast cell, whose capacity to respond and trigger the inflammatory process is in the order of microseconds. The activation thereof generates a series of reactions resulting in the release of preformed mediators contained within the cytoplasm thereof; in rapid succession, the macrophages are recalled and then activated.

The function of the macrophages is structured over two phases: the first, known as M1, involves the activation of a series of reactions resulting in the release into the microenvironment of chemical mediators, such as NGF (Nerve Growth Factor), VEGF (Vascular Endothelial Growth Factor), FGF (Fibroblast Growth Factor), histamine, interleukins, cytokines, and lipid products, such as arachidonic acid, prostaglandins and heparin, which are able to trigger and support the inflammatory process, as well as to "attract" the other cells in the immune system to the site of inflammation. The second phase, known as M2, involves the activation of the 'scavenger' phenomenon (cleaning phenomenon), which is aimed at eliminating the waste resulting from the destruction of the agent responsible for the inflammatory action. Between the macrophage activation phase in M1 and M2, the basophils—whose role is to release histamine into the microenvironment subjected to the aggression of the inflammatory agent—are attracted and activated, leading to vasodilation and, consequently, oedema, as a result of immune cell diapedesis or extravasation. When the inflammatory reaction has reached the diapedesis phase, the lymphocytes—whose role is to counteract the pathogenic agent—reach the area. The entire inflammatory process is triggered in just a few microseconds.

All complex biological systems are regulated by a system of opposition based on agonism and antagonism mechanisms. More generally, the degranulation of the mast cell mediators triggers a series of phenomena which are synthesised during the inflammatory process. The aforesaid cells in the immune system are self-regulated by means of fine receptor mechanisms involving a sophisticated system of receptors, expressed in the cytoplasmic membrane, which can be overexpressed during stimulation processes. This overexpression determines a release, within the extra-cellular space, of a series of chemical mediators, which trigger a series of events whose purpose is to defend the tissue microenvironment and bring about repair phenomena. The system is regulated by the production of receptor antagonists, which are produced by the cell itself, from fatty acids taken from the cell membrane.

These biological systems are based on receptor control: following stimulation of the pathogenic agent, the cells express specific receptors which are saturated with self-produced mediators, i.e. formed from the fatty acids constituting the membranes of the said cells. The expression of receptors is the means by which the cells involved in the inflammatory process are able to transfer growth factors, interleukins, cytokines, etc., into the microenvironment. The saturation of these receptors allows first the reduction and then the modulation of the degranulation of the mediators present within the cytoplasm of the cells involved in the inflammatory process (the mast cells in particular), until the stimulation induced by the presence of the pathogenic agent is halted. This regulation system, however, comes to an end when the continuous dwindling of the fatty acids in the cell membranes causes suffering to the said cell. In this condition, the receptors are overexpressed and, for the cell, this constitutes a degranulation signal aimed at the mediators that trigger defence phenomena which are no longer necessary.

Therefore, if there were no receptor control, the cells would obviously induce the degranulation of all the mediators present in the cytoplasm, leading to the other cells being recalled to the microenvironment. This would then lead to an irritation of the system, which—remaining active—could become a source of damage, giving rise to chronic inflammatory pathologies and autoimmune diseases, such as rheumatoid arthritis, multiple sclerosis, and systemic lupus erythematosus.

At present, the pharmacological therapies used for inflammatory pathologies include corticosteroids (such as cortisone and analogue substances) or NSAIDs (non-steroidal anti-inflammatory drugs), which act on different levels of the arachidonic acid cascade.

Corticosteroids counteract the formation of arachidonic acid from phospholipids through the inhibition of the phospholipase activity, including phospholipase A2 (PLA2) and phospholipase C (PLC). In particular, the mechanism by which corticosteroids exert their anti-inflammatory and immunosuppressive action is highly structured and involves several biochemical processes implemented by cell in response to potentially harmful stimuli (e.g. infectious agents, allergens, foreign substances, abnormal cells, etc.).

The role of this mechanism is to trigger an immune response, maintain it until the risk is eliminated and then deaden the response so that it does not go on to become harmful (as happens, for example, in chronic inflammation cases or autoimmune diseases). In particular, the corticosteroids inhibit the cellular processes that lead to the synthesis of pro-inflammatory and immunostimulatory substances and, vice versa, activate the cellular processes that lead to the synthesis of anti-inflammatory and immunosuppressive substances, in order to reduce the symptoms of the disease.

Apart from the anti-inflammatory/immunosuppressive effect, the side effects of the synthesised corticosteroids generally stem from the fact that they interfere with the body's homeostatic systems and therefore may cause: hypertension, water retention, hyperglycaemia, potassium loss, osteoporosis, muscle hypertrophy, capillary fragility, delayed wound healing, hyperlipidaemia, accumulation of adipose tissue in the face, neck and abdomen, gastroduodenal ulcers, increased blood coagulability, haematological disorders, euphoria, and insomnia.

In prolonged treatment, moreover, these pharmacological substances tend to inhibit the production of analogue natural hormones by the adrenal glands, thereby causing a situation of adrenal insufficiency, which occurs with serious consequences, especially upon discontinuation of the therapy. Furthermore, prolonged use of corticosteroids is linked to the immunosuppressive action thereof, which increases susceptibility to infections.

NSAIDs, meanwhile, interfere with the arachidonic acid cascade on a different level, by inhibiting cyclooxygenases COX1 and 2, which are involved in inflammatory processes. The most common side effects are those affecting the digestive system, in particular, the stomach, and include pain, burning sensations, or nausea, and ulceration of the gastric mucosa with possible bleeding; as well as skin reactions in susceptible individuals (erythema, urticaria).

Therefore, there is a need to identify one or more active ingredients for the treatment of inflammation which can effectively modulate hyperactivity of the inflammatory process, reducing the side effects associated with conventional treatments.

It is, therefore, extremely important to provide the cells of the tissue which has suffered noxae not only with elements capable of controlling the inflammatory reactions, through control of the cells involved, but also to provide the tissue with all the elements required for the rapid recovery of the specific homeodynamic balance of the tissue in question.

Surprisingly, it has now been found that the combination of spirulina and palmitoylethanolamide (PEA) and/or pharmaceutically acceptable derivates or salts thereof is able to prevent and/or efficiently treat tissue hyperactivation states and, in particular, to prevent and/or efficiently treat inflammatory states.

Spirulina is a unicellular micro-seaweed which grows in fresh water, salt water, and brackish waters and grows best in a highly alkaline environment with a pH of 10-12. Spirulina has been used as a food source for centuries (and is still commonly consumed in Chad and other African countries) as it is popularly known as a "superfood" (www.i-imsam.org) due to the wide variety and concentration of nutrients contained therein.

Spirulina is marketed as a dietary supplement or as an active ingredient of functional foods and beverages, since the said organism is composed, among other things, of highly digestible proteins which can provide all the essential amino acids. Furthermore, spirulina contains more beta-carotene than any other whole food, is the best whole food source of gamma-linolenic acid (GLA), and is rich in B-group vitamins, minerals, trace elements, chlorophyll, and enzymes. Finally, it abounds with other nutrients, such as carotenoids, sulpholipids, glycolipids, phycocyanins and superoxide dismutase.

The multiple effects of spirulina, which are widely documented in literature, include (to cite an example) anti-inflammatory and anti-oxidant activity (Gemma C, et al., J. Neurosci (2002), 22 (14): 6114-20), protective activity in relation to the liver and kidneys (R. Samuels et al., J Med Food. (2002), 5(2): 91-6), ameliorative activities of the lipid panel (Nagaoka et S. al., J. Nutr. (2005), 135(10): 2425-30), protective activity against infection (Hernandez-Crown A. et al., Antiviral Res (2002), 56(3): 279-85), protective activity for the cardiovascular system (Khan M. et al., Am J Physiol Heart Circ Physiol. (2006), 290(5): H2136-45. Epub 2005 Dec. 22) and protective activity for the cerebral system (Wang Y. et al., Exp Neurol. (2005), 193(1): 75-84) and carcinogenesis control activities (Akao Y. et al., Cancer Sci. (2009), 100(8):1494-501, Epub 2009 May 6).

Palmitoylethanolamide (PEA), a molecule which has long been approved as a "dietary food for special medical purposes, to be used under medical supervision" in many countries, is a natural substance with a lipid nature and N-acylethanolamine structure, which is contained in many foods commonly used for human consumption and, in particular, in vegetable oils of various origins, egg yolk, soy beans, peas, sweet vetch (Vicia sativa), and oat grains.

In 1957, it was isolated for the first time in the pure state and characterised, from egg yolk and from soybean (Kuehl et al., Journal of the American Chemical Society, (1957), 79 (19): 5577-5578) after which, in 1954, it was demonstrated that diets based on egg yolk or certain lipid fractions extracted from the said egg yolk and added as supplements to normal diets could improve the characteristic symptoms of arthritis anaphylactic which affect joints (A F Coburn et al., J Exp Med. (1954), 100(5): 425-35).

The biological mechanisms for the synthesis and breakdown of palmitoylethanolamide in the human body have been widely studied and are known perfectly today, as are the processes for the breakdown thereof: indeed, a ubiquitous hydrolase-specific starch has been isolated, which can break the acyl amide bond, releasing palmitic acid and ethanolamine. Both components of the molecule are subsequently reused in the metabolic cycle of phospholipids (Ueda N. et al., J Biol Chem. (2001), 276(38): 35552-7. Epub 2001).

The physiological presence of PEA has been detected in various mammalian organs; in humans, this particular lipid is present in many organs, in particular, in the central and peripheral nervous system, the skin, spleen, and in plasma. The physiological levels of PEA are regulated, in the organism, according to the various cellular stresses; it has been observed that endogenous synthesis of the lipid increases strongly when cellular stress is induced experimentally in certain organs in laboratory animals. In humans and animals with pathological conditions involving cellular suffering and consequential tissue hyperreactivity states, significant changes in endogenous levels of PEA have been evidenced (Matias I. et al., Biochim Biophys Acta (2008), 1781(1-2): 52-60. Epub 2007). The conclusion of research into the biological significance of the presence of PEA and the function thereof in the body is that the aforesaid compound intervenes physiologically to keep tissue responsiveness within limits which are compatible with the regional homeodynamic balance.

Definitions

Unless otherwise defined, when used herein, all the terms used in the art, and likewise the notations and other scientific terms, are intended as having the meanings commonly understood by those skilled in the art to which this description belongs. In some cases, terms with commonly understood meanings are defined herein for the sake of clarity and/or for ease of reference; the inclusion of such definitions herein should not, therefore, be interpreted as intending a substantial difference with respect to that which is generally understood in the art.

According to the present invention, the term "physiologically acceptable excipient" refers to a substance devoid of any pharmacological effect of its own and which does not produce adverse reactions when administered to a mammal, preferably a human being. Physiologically acceptable excipients are well known in the art and are described, for example, in the Handbook of Pharmaceutical Excipients, sixth edition (2009), which has been incorporated herein for reference purposes.

According to the present invention, the term "salts or pharmaceutically acceptable derivates" refers to those salts or derivates which have the biological effectiveness and the properties of the salified or derivate compound and which do not produce adverse reactions when administered to a mammal, preferably a human being. The pharmaceutically acceptable salts may be inorganic or organic salts; examples of pharmaceutically acceptable salts include, but are not limited to: carbonate, hydrochloride, hydrobromide, sulphate, hydrogen sulphate, citrate, maleate, fumarate, trifluoroacetate, 2-naphthalenesulfonate, and paratoluenesulfonate. More information on the pharmaceutically acceptable salts can be found in the Handbook of pharmaceutical salts, P. Stahl, C. Wermuth, Wiley-VCH, 127-133, 2008, incorporated herein for reference purposes. The pharmaceutically acceptable derivates include esters, ethers, and N-oxides.

The term "simultaneous, separate, or sequential use" refers to the simultaneous administration of the first and second compound, or administration in such a way that the two compounds act in the patient's body simultaneously or administration of one compound after the other compound so as to provide a therapeutic effect. In some embodiments, the compounds are taken with a meal. In other embodiments, the compounds are taken after a meal, for example 30 minutes or 60 minutes after the meal. In some embodiments, a compound is administered to a patient for a period of time, followed by administration of the other compound. The terms "comprising", "having", "including" and "containing" should be understood as 'open' terms (i.e. meaning "including, but not limited to") and should also be deemed a support for terms such as "consist essentially of", "consisting essentially of", "consist of", or "consisting of".

DESCRIPTION

Surprisingly, it has now been found that the combination of spirulina and palmitoylethanolamide (PEA) and/or pharmaceutically acceptable derivates or salts thereof can prevent and/or efficiently treat tissue hyperactivation states.

In particular, the combination of spirulina and PEA is useful in the prevention and/or treatment of inflammatory pathologies, in the prevention and/or treatment of alterations in cardiac and/or coronary tissue, in the prevention and/or treatment of alterations in vascular tissue, in the prevention and/or treatment of ophthalmic pathologies, and preferably in the prevention and/or treatment of macular degeneration and/or glaucoma, in the prevention and/or treatment of dyslipidemia, in the prevention and/or treatment of alterations in pulmonary tissue, in the prevention and/or treatment of alterations in pelvic tissues, in the prevention and/or treatment of cellular alterations due to carcinogenesis, and/or in the prevention and/or treatment of dermatological alterations.

One object of the present invention is therefore a combination comprising spirulina and PEA, and/or pharmaceutically acceptable derivates or salts thereof. Preferably, the spirulina used in the present invention is a dry extract.

According to a preferred aspect, the percentage of spirulina and/or pharmaceutically acceptable derivates or salts thereof is between 10% and 90% of the combination, wherein the percentage of PEA and/or pharmaceutically acceptable derivates or salts is between 10% and 90% of the combination, wherein the said percentages refer to the total weight of the combination.

Particularly preferred combinations are those comprising spirulina and PEA and/or pharmaceutically acceptable derivates or salts thereof wherein the percentages of spirulina and PEA in the combination are, respectively: 65% and 35%, or 55% and 45%, or 70% and 30%, or 35% and 65%, or 40% and 60%, wherein the said percentages refer to the total weight of the combination.

A further object of the present invention consists of the combination comprising spirulina and PEA, and/or pharmaceutically acceptable derivates or salts thereof, for use in the prevention and/or treatment of tissue hyperactivation states, in the prevention and/or treatment of inflammatory pathologies, in the prevention and/or treatment of alterations in the central nervous system (CNS) and the peripheral nervous system (PNS), preferably in the degeneration of central nervous tissue, such as for example, tinnitus, and in degenerative pathologies, in the prevention and/or treatment of loss of cognitive ability due to degenerative and/or traumatic causes, in the prevention and/or treatment of disorders of the peripheral nervous system, as well as in the prevention and treatment of peripheral neuropathies, in the prevention and/or or treatment of alterations in cardiac tissue and/or coronary, in the prevention and/or treatment of alterations in the vascular tissue, in the prevention and/or treatment of ophthalmic pathologies, preferably in the prevention and/or treatment of macular degeneration and glaucoma, in the prevention and/or treatment of dyslipidemia, in the prevention and/or treatment of alterations in pulmonary tissue, in the prevention and/or treatment of alterations in the renal tissue, in the prevention and/or treatment of alterations in the pelvic tissues, in the prevention and/or treatment of cellular alterations due to carcinogenicity, and/or in the prevention and/or treatment of dermatological alterations.

The aforesaid alterations in cardiac tissue may be due to ischemia, heart attack, and/or surgical procedures in the past and/or in progress.

The aforesaid alterations in coronary tissue may be due to stenosis, occlusions, hormonal alterations, tissue degeneration and/or surgical procedures in the past and/or in progress.

The aforesaid alterations in vascular tissue may be due to infections, hormonal alterations, tissue degeneration and/or surgical procedures in the past and/or in progress.

The aforesaid alterations in renal tissue may be due to infections, hormonal alterations, tissue degeneration and/or surgical procedures in the past and/or in progress.

The aforesaid alterations in pulmonary tissue may be due to allergic processes, infections, tissue degeneration (including therein degeneration of oncological origin) in the past and/or in progress.

The aforesaid alterations in tissue in the pelvic area may be due to allergic processes, infections, hormonal alterations, tissue degeneration and/or surgical procedures in the past and/or in progress.

The aforesaid alterations in the central nervous system tissue may be due to degenerative processes, alterations in nerve conduction, alterations of oncological or hormonal origin, tissue degeneration, and/or surgical procedures in the past and/or in progress.

The aforesaid alterations in the peripheral nervous system tissue may be due to degenerative processes, alterations in nerve conduction, alterations of oncological or hormonal origin, tissue degeneration, and/or surgical procedures in the past and/or in progress.

The combination in the invention, as defined above, is useful for the treatment of alterations after the reperfusion of cardiac tissue following heart attacks, coronary occlusion, and/or surgical procedures.

Without being bound to a particular theory, it is thought that the synergistic action of the combination comprising spirulina and PEA, and/or pharmaceutically acceptable derivates or salts thereof, is due both to the regulatory activity of the PEA in relation to the inflammatory process and that of the spirulina in relation to the immune system cells during the immune system cell hyperactivation processes, in the same way as occurs during the inflammatory processes. Spirulina may also provide the tissue cells involved in the hyperactivation with a series of elements such as protein, vitamins, fatty acids, minerals, etc. which can support the functional recovery of the tissue involved. The aforesaid tissue alterations may be acute or chronic and may be dermatological pathologies, such as atopic dermatitis, dermatomyositis, scleroderma, psoriasis, polymyositis, pemphigus, epidermolysis bullosa, and pemphigoid; ophthalmic pathologies, such as, for example, Sjogren's syndrome, sympathetic ophthalmia, uveitis, uveo-retinitis, macular degeneration, optic neuritis and glaucoma; mucosal pathologies, such as those of the gastrointestinal mucous membranes (Crohn's disease) and the oral and genital mucosa; articular and connective pathologies, such as rheumatoid arthritis, psoriatic arthritis, arthritis from lupus erythematosus, and discoid and systemic lupus erythematosus; pathologies, such as chronic solar dermatitis, asthma, and intestinal and pulmonary fibrosis, and chronic arthritis; degenerative pathologies of the peripheral nervous system (PNS) and central nervous system (CNS), such as multiple sclerosis, neurodegenerative pathologies (not only of the autoimmune variety), processes connected to the CNS, such as Parkinson's disease, senile dementia, bacterial meningitis, HIV infections, tinnitus, Meniere's syndrome, brain damage of ischemic or hemorrhagic origin and traumatic damage; pathologies of the PNS, such as radiculopathy of inflammatory origin; pathologies of the central and peripheral nervous system where the inflammatory processes follow the first ischemic insult, such as neuropathies due to compression, as well as traumatic neuropathies, cerebral strokes and cranial traumas; cardiological diseases deriving from perfusion phenomena as a consequence of ischemic injuries; pathologies associated with fibrosis, such as allergic conjunctivitis, giant papillary conjunctivitis, dietary allergies, abnormal cicatrisation, such as hypertrophic cicatrix, keloids, and ocular cicatricial pemphigoid; pathologies in which renal function is altered as a result of alterations in renal functions.

In particular, the combination comprising spirulina and PEA, and/or pharmaceutically acceptable salts or derivates thereof, is for simultaneous, separate, or sequential use in the prevention and/or treatment of the aforesaid pathologies. In other words, the active ingredients of the combination envisaged in the invention may be administered simultaneously, separately, or sequentially.

A further object of the present invention is a composition comprising the combination of spirulina and PEA and/or pharmaceutically acceptable derivatives or salts thereof, optionally together with at least one physiologically acceptable excipient.

The compositions comprising the combination of spirulina and PEA and/or pharmaceutically acceptable derivates or salts thereof, optionally together with at least one physiologically acceptable excipient, are suitable for use in the prevention and/or treatment of all the aforesaid pathologies for the combination of spirulina and PEA and/or pharmaceutically acceptable derivates or salts thereof. Preferably, the said combinations are for simultaneous, separate, or sequential use in the prevention and/or treatment of all the aforesaid pathologies.

According to preferred embodiments of the present invention, the said compositions comprising the combination in the invention together with a pharmaceutically acceptable excipient are compositions which are administrable in oral, topical, otologic, ophthalmic, rectal, vaginal, or parenteral forms.

Preferably, when the administration of the compositions in the invention is performed orally, the pharmaceutical form may be a tablet, capsule, granules, powder, oily capsule, solution or a suspension, and still more preferably, the said oral form may be a tablet, capsule, granules, or a solution.

Preferably, when the administration of the compositions in the invention is performed topically, the pharmaceutical form may be a cream, ointment, gel, salve, solution, wash (solution or suspension), drops, buffer (buffer solution), suspension, eye drops, spray, wipe, or powder, and more preferably, the said topical form may be a cream, gel, spray, suppository, or an ointment.

The topical forms of administration may also include otologic topical administration, and in this case the pharmaceutical form may be a wash, spray, drops, buffer or cream, and ophthalmic administration, in which case the pharmaceutical form may be eye drops, wash, wipe, or cream.

Preferably, when the administration of the compositions in the invention is performed rectally, the pharmaceutical form may be a cream, suppository, or an enema.

Preferably, when the administration of the compositions in the invention is performed vaginally, the pharmaceutical form may be a cream, pessary, wipe or a cannula.

Preferably, when the administration of the compositions in the invention is performed parenterally, the pharmaceutical form may be an aqueous buffer solution or oily suspension capsule, and still more preferably, the said parenteral form may be an oily solution.

Still more preferably, when the combination and/or the compositions according to the invention are used in the prevention and/or treatment of alterations in cardiac tissue, the following pharmaceutical forms are preferred: tablet, capsule, powder, solution, or wash.

Still more preferably, when the combination and/or the compositions according to the invention are used in the prevention and/or treatment of alterations in vascular tissue, the following pharmaceutical forms are preferred: capsule, powder, solution, tablet, cream, gel, or ointment.

Still more preferably, when the combination and/or the compositions according to the invention are used in the prevention and/or treatment of alterations in coronary tissue, the following pharmaceutical forms are preferred: capsule, powder, solution, or tablet.

Still more preferably, when the combination and/or the compositions according to the invention are used in the prevention and/or treatment of alterations after reperfusion of cardiac tissue, the following pharmaceutical forms are preferred: capsule, powder, solution, or tablet.

Still more preferably, when the combination and/or the compositions according to the invention are used in the prevention and/or treatment of dyslipidemia, the following pharmaceutical forms are preferred: capsule, powder, solution, or tablet.

Still more preferably, when the combination and/or the compositions according to the invention are used in the prevention and/or treatment of cellular alterations, the following pharmaceutical forms are preferred: powder, solution, tablet, cream, ointment, pessary, suppository, or wash.

Still more preferably, when the combination and/or the compositions according to the invention are used in the prevention and/or treatment of alterations in pulmonary tissue, the following pharmaceutical forms are preferred: capsule, powder, solution, tablet, or spray.

Still more preferably, when the combination and/or the compositions according to the invention are used in the prevention and/or treatment of alterations in tissue in the pelvic area, the following pharmaceutical forms are preferred: capsule, powder, solution, tablet, wash, spray, cream, pessary, enema, gel or ointment.

Still more preferably, when the combination and/or the compositions according to the invention are used in the prevention and/or treatment of alterations in central nervous system (CNS) tissue and/or peripheral nervous system (PNS) tissue, the following pharmaceutical forms are preferred: capsule, powder, solution, tablet, wash, spray, cream, pessary, enema, gel or ointment.

Still more preferably, when the combination and/or the compositions according to the invention are used in the prevention and/or treatment of alterations in renal tissue, the following pharmaceutical forms are preferred: capsule, powder, solution, tablet, wash, spray, cream, pessary, enema, gel or ointment.

According to a preferred embodiment of the present invention, the formulations comprising the combination of spirulina and palmitoylethanolamide (PEA) and/or pharmaceutically acceptable derivates or salts thereof, optionally together with at least one physiologically acceptable excipient, are administered daily.

According to a preferred aspect, the daily administration envisages one to four doses per day, even more preferably two or four daily doses, wherein the said doses preferably contain from 0.1 to 90 mg of the combination in the invention per kg of the patient's body weight, and still more preferably from 0.5 to 50 mg per kg of the patient's body weight.

According to a further preferred aspect of the invention, daily administration is continued for a period of at least 15 days, preferably of at least 30 days, and still more preferably of at least 90 days. According to a further preferred aspect, such administration is continued for a period of at least 35 days, preferably for at least 65 days.

According to a still further preferred embodiment of the present invention, the composition in the invention is administered orally, preferably in the form of a tablet or capsule, twice or four times a day, for a period of at least 15 days, preferably at least 30 days, and still more preferably, at least 90 days. According to a further preferred aspect, such administration is continued for a period of at least 35 days, preferably for at least 65 days.

According to a further preferred aspect, each of the aforesaid tablets comprises from 200 to 700 mg of PEA and from 300 to 800 mg of spirulina, and more preferably comprises 300, 350, 450, 600 or 650 mg of PEA and 350, 400, 550, 650 or 700 mg of spirulina.

Still more preferably, the aforesaid tablets contain 350 mg of PEA and 650 mg of spirulina, or they contain 450 mg of PEA and 550 mg of Spirulina, or they contain 300 mg of PEA and 700 mg of spirulina, or they contain 650 mg of PEA and 350 mg of spirulina, or they contain 600 mg of PEA and 400 mg of spirulina.

Example 1

A clinical study was performed to test the synergistic effect of the combination of spirulina (used as dry extract) and palmitoylethanolamide (PEA) in the treatment of tinnitus.

In the study, six patients were treated, comprising both men and women, with a mean age of 49.6 years (50-year-old woman, 46 year-old man, 38 year-old man, 46 year-old woman, 53 year-old man, 65 year-old women), who had been suffering from tinnitus for at least one year.

The patients were divided into three groups and, in accordance with the present invention, were treated according to the following schema:
  the patients in the first group (aged 46 to 50 years) were treated with two tablets, each comprising 350 mg of PEA, administered twice a day, for a daily total of 1,400 mg of PEA, for a duration of 5 days; next, the same patients were treated with one tablet, comprising 350 mg of PEA, administered twice a day, for a daily total of 700 mg of PEA, for a duration of 10 days;
  the patients in the second group (aged 38 to 53 years) were treated with two tablets, each comprising 650 mg of spirulina, administered twice a day, for a daily total of 2,600 mg of spirulina, for a duration of 5 days; next, the same patients were treated with one tablet, comprising 650 mg of spirulina, administered twice a day, for a daily total of 1,300 mg of spirulina, for a duration of 10 days;

the patients in the third group (aged 46 to 65 years) were treated with two tablets, each comprising 650 mg of spirulina and 350 mg of PEA, administered twice a day, for a daily total of 2,600 mg of spirulina combined with 1,400 mg of PEA, for a duration of 5 days; next, the same patients were treated with one tablet, comprising 650 mg of spirulina and 350 mg of PEA, administered twice a day, for a daily total of 1,300 mg of spirulina combined with 700 mg of PEA, for a duration of 10 days;

All the patients received the products for the period stated.

At the examination after the treatment, neither the two patients treated with PEA, nor the two patients treated with spirulina showed variations in the tinnitus, while the two patients treated with the combination of spirulina and PEA (where the spirulina totalled 65% of the combination and the PEA 35%) showed a marked and significant improvement in the tinnitus perceived, with an approximately 65% reduction in the tinnitus and a marked improvement in hearing. The improvements regarding the tinnitus were declared by patients, while the improvement in hearing was measured via an audiometric test, carried out before and after administration of the combination in the invention. It is particularly significant that the 65% reduction in tinnitus was obtained among patients who had been suffering from the pathology for a long time.

The synergistic effect of the combination of spirulina and PEA in the treatment of tinnitus has therefore been demonstrated, in particular where the combination comprises 65% spirulina and 35% PEA.

Example 2

A clinical study was performed to test the synergistic effect of the combination of spirulina (used as dry extract) and PEA in the treatment of senile macular degeneration.

In the study, three patients were treated, comprising both men and women, aged 56 years, 65 years and 62 years, who were suffering from age-related macular degeneration with the presence of macular drusen, i.e. localised deposits between the retinal pigment epithelium (RPE) and the Bruch membrane, together with geographic atrophy, characterised by RPE cell death and atrophy of the overlying photoreceptors.

All the patients underwent an assessment with the Amsler test, prior to administration of the combination of spirulina and PEA. All three patients presented macular degeneration with distortion (metamorphopsia) or line breaks with an average degree of macular degeneration.

In accordance with the present invention, the patients were treated according to the following schema:
  the first patient (65-year-old man) was treated with a tablet comprising 450 mg of PEA, administered four times a day, for a daily total of 1,800 mg of PEA, for a duration of 10 days; next, the same patient was treated with one tablet, comprising 450 mg of PEA, administered twice a day, for a daily total of 900 mg of PEA, for a duration of 30 days;
  the second patient (56-year-old woman) was treated with a tablet comprising 550 mg of spirulina, administered four times a day, for a daily total of 2,200 mg of spirulina, for a duration of 10 days; next, the same patient was treated with one tablet, comprising 550 mg of spirulina, administered twice a day, for a daily total of 1,100 mg of spirulina, for a duration of 30 days;
  next, the third patient (62-year-old man) was treated with one tablet, comprising 550 mg of spirulina and 450 mg of PEA, administered four times a day, for a daily total of 2,200 mg of spirulina combined with 1,800 mg of PEA, for a duration of 10 days; next, the same patient was treated with one tablet, comprising 550 mg of spirulina and 450 mg of PEA, administered twice a day, for a daily total of 1,100 mg of spirulina combined with 900 mg of PEA, for a duration of 30 days.

All the patients received the products for the period stated.

Following treatment, all the patients underwent a further Amsler test, which produced the following results:
  the patient undergoing treatment with PEA showed a slight improvement in the Amsler test result;
  the patient undergoing treatment with spirulina showed a very slight improvement in the Amsler test result;
  the patient undergoing treatment with the combination of spirulina and PEA (where the spirulina totalled 55% of the combination and the PEA 45%) showed a clear, marked improvement in the Amsler test result, with—furthermore—an improvement in sight.

The synergistic effect of the combination of spirulina and PEA in the treatment of senile macular degeneration has therefore been demonstrated, in particular where the combination comprises 55% spirulina and 45% PEA.

Example 3

A clinical study was performed to test the synergistic effect of the combination of spirulina (used as dry extract) and PEA in the treatment of angina pectoris (chest pain).

In the study, three patients were treated, comprising both men and women, aged 67, 65, and 72 years, who suffered from praecordial pain of cardiac origin. Upon undergoing a stress ECG, all the patients presented anginal pain during the stress and all were undergoing specific treatments (antihypertensives, beta blockers), which—nevertheless—were unable to fully control the aforesaid symptoms.

In accordance with the present invention, the patients were treated according to the following schema:
  the first patient (65-year-old woman) was treated with a tablet comprising 300 mg of PEA, administered four times a day, for a daily total of 1,200 mg of PEA, for a duration of 15 days; next, the same patient was treated with one tablet, comprising 300 mg of PEA, administered twice a day, for a daily total of 600 mg of PEA, for a duration of 30 days;
  the second patient (67-year-old man) was treated with a tablet comprising 700 mg of spirulina, administered four times a day, for a daily total of 2,800 mg of spirulina, for a duration of 15 days; next, the same patient was treated with one tablet, comprising 700 mg of spirulina, administered twice a day, for a daily total of 1,400 mg of spirulina, for a duration of 30 days;
  next, the third patient (72-year-old man) was treated with one tablet, comprising 700 mg of spirulina and 300 mg of PEA, administered four times a day, for a daily total of 2,800 mg of spirulina combined with 1,200 mg of PEA, for a duration of 15 days; next, the same patient was treated with one tablet, comprising 700 mg of spirulina and 300 mg of PEA, administered twice a day, for a daily total of 1,400 mg of spirulina combined with 600 mg of PEA, for a duration of 30 days.

All the patients received the products for the period stated in addition to the treatments already underway.

Following treatment, the patients produced the following results:
- the patient being treated solely with PEA showed no significant changes in condition with respect to prior to administration of the PEA, i.e. when stress was increased during the stress ECG, the patient presented praecordial pain of cardiac origin;
- the patient being treated solely with spirulina showed very slight changes in condition with respect to prior to administration of the spirulina, i.e. when stress was increased during the stress ECG, the patient presented a lesser degree of praecordial pain of cardiac origin;
- the patient being treated with the combination of spirulina and PEA (where the spirulina amounted to 70% of the combination and PEA amounted to 30%) showed a clearly improved capacity to endure the stress ECG, without the appearance of praecordial pain, with respect to prior to administration of the combination in the invention. In particular, the improved capacity to endure the stress demonstrates the functional recovery of the heart muscle, accompanied by a net reduction in pain symptoms.

The synergistic effect of the combination of spirulina and PEA in the treatment of angina pectoris (chest pain) has therefore been demonstrated, in particular where the combination comprises 70% spirulina and 30% PEA.

Example 4

A clinical study was performed to test the synergistic effect of the combination of spirulina (used as dry extract) and PEA in the treatment of peripheral neuropathy in diabetics.

In the study, three patients were treated, comprising both men and women, aged 52, 58, and 62 years, who suffered from peripheral neuropathy of diabetic origin. All the patients presented the classic symptoms of peripheral neuropathy, i.e. the classic symptoms consisting of paraesthesias, the sensation of 'walking on cotton wool', insensitivity to heat and/or cold, etc., and all the patients were undergoing specific treatments to control glycaemic values, in particular oral hypoglycaemic agents. The patients' glycaemia was tested, both at the beginning and the end of the study, to see if taking the product influenced glycaemic control in any way. All the patients had mean fasting glycaemia values of approximately 140 to 165 mg/dl.

In accordance with the present invention, the patients were treated according to the following schema:
- the first patient (52-year-old man) was treated with a tablet comprising 650 mg of PEA, administered four times a day, for a daily total of 2,600 mg of PEA, for a duration of 5 days; next, the same patient was treated with one tablet, comprising 650 mg of PEA, administered twice a day, for a daily total of 1,300 mg of PEA, for a duration of 30 days;
- the second patient (58-year-old woman) was treated with a tablet comprising 350 mg of spirulina, administered four times a day, for a daily total of 1,400 mg of spirulina, for a duration of 5 days; next, the same patient was treated with one tablet, comprising 350 mg of spirulina, administered twice a day, for a daily total of 700 mg of spirulina, for a duration of 30 days;
- next, the third patient (62-year-old man) was treated with one tablet, comprising 350 mg of spirulina and 650 mg of PEA, administered four times a day, for a daily total of 1,400 mg of spirulina combined with 2,600 mg of PEA, for a duration of 5 days; next, the same patient was treated with one tablet, comprising 350 mg of spirulina and 650 mg of PEA, administered twice a day, for a daily total of 700 mg of spirulina combined with 1,300 mg of PEA, for a duration of 30 days.

All the patients received the products for the period stated.

Following treatment, the patients produced the following results, which were assessed by measuring nerve conduction using a neurological tuning fork, biothesiometer, and via the Achilles reflex:
- the patient undergoing treatment solely with PEA showed a slight improvement in the neuropathic symptoms, without any influence on the glycaemic profile, and with a slight response to the biothesiometry test (glycaemic values remained constant, i.e. 140-160 mg/dl when fasting);
- the patient undergoing treatment solely with spirulina showed no changes in either the neuropathic condition or the glycaemic profile. Indeed, the initial assessment parameters with the tuning fork, the biothesiometer and the Achilles reflex test, remained unchanged, as did the glycaemic value, which was in the range of 155-160 mg/dl;
- the patient undergoing treatment with the combination of spirulina and PEA (where the spirulina totalled 35% of the combination and the PEA 65%) showed a clear improvement in the characteristic symptoms of peripheral neuropathy, with a clear improvement in nerve conduction and an improved glycaemic profile. In fact, the patient showed a marked improvement in nerve conduction when assessed with the tuning fork and the biothesiometer and a clear improvement in the Achilles reflex and glycaemic values showed an improvement, decreasing from a fasting value of 140-160 mg/dl to a fasting value of 130-140 mg/dl.

The synergistic effect of the combination of spirulina and PEA in the treatment of peripheral neuropathy in diabetics has therefore been demonstrated, in particular where the combination comprises 35% spirulina and 65% PEA.

Example 5

A clinical study was performed to test the synergistic effect of the combination of spirulina (used as dry extract) and PEA in the treatment of altered renal functions, preferably in diabetics.

In the study, three patients were treated, comprising both men and women, aged 52, 58, and 62 years, who suffered from diabetes. All patients presented altered renal functions, evidenced by the creatinine value, i.e. a creatinine value of over 4 mg/dl (normal values range from 0.7 to 1.3 mg/dl). All the patients were undergoing specific treatments (conventional drugs, such as Decadurabolin, etc.) which, nevertheless, were unable to control the renal dysfunction. The patients' creatinine values were tested, both at the beginning and the end of the clinical study assessment.

In accordance with the present invention, the patients were treated according to the following schema:
- the first patient (52-year-old man) was treated with a tablet comprising 650 mg of PEA, administered four times a day, for a daily total of 2,600 mg of PEA, for a duration of 5 days; next, the same patient was treated with one tablet, comprising 650 mg of PEA, administered twice a day, for a daily total of 1,300 mg of PEA, for a duration of 30 days;
- the second patient (58-year-old woman) was treated with a tablet comprising 350 mg of spirulina, administered four times a day, for a daily total of 1,400 mg of spirulina, for a duration of 5 days; next, the same patient was treated with one tablet, comprising 350 mg of spirulina, administered twice a day, for a daily total of 700 mg of spirulina, for a duration of 30 days;

next, the third patient (62-year-old man) was treated with one tablet, comprising 350 mg of spirulina and 650 mg of PEA, administered four times a day, for a daily total of 1,400 mg of spirulina combined with 2,600 mg of PEA, for a duration of 5 days; next, the same patient was treated with one tablet, comprising 350 mg of spirulina and 650 mg of PEA, administered twice a day, for a daily total of 700 mg of spirulina combined with 1,300 mg of PEA, for a duration of 30 days.

All the patients received the products for the period stated.

After treatment, the patients showed the following creatinine values, which are indicative of renal functions:

the patient undergoing treatment solely with PEA showed no improvement in renal functions, as the patient's creatinine values were: 4.3 mg/dl at the beginning of the treatment and 4.4 mg/dl at the end of the treatment;

the patient undergoing treatment solely with spirulina showed no changes in the condition of the renal functions, as the patient's creatinine values were: 4.5 mg/dl at the beginning of the treatment and 4.6 mg/dl at the end of the treatment;

the patient undergoing treatment with the combination of spirulina and PEA (where the spirulina amounted to 35% of the combination and the PEA amounted to 65%) showed a clear improvement in renal functions (renal filtering), as the patient's creatinine values were: 4.6 mg/dl at the beginning of the treatment and 4.1 mg/dl at the end of the treatment;

The synergistic effect of the combination of spirulina and PEA in the treatment of altered renal functions, preferably in diabetic subjects, has therefore been demonstrated, in particular where the combination comprises 35% spirulina and 65% PEA.

The invention claimed is:

1. A pharmaceutical composition consisting essentially of a combination of spirulina and palmitoylethanolamide, wherein the percentage of spirulina is between 10% and 90% of the combination and the percentage of palmitoylethanolamide is between 10% and 90% of the combination.

2. A pharmaceutical composition according to claim 1 together with at least one physiologically acceptable excipient.

* * * * *

UNITED STATES PATENT AND TRADEMARK OFFICE
CERTIFICATE OF CORRECTION

| | |
|---|---|
| PATENT NO. | : 10,646,523 B2 |
| APPLICATION NO. | : 15/519611 |
| DATED | : May 12, 2020 |
| INVENTOR(S) | : Raffaele Migliaccio, Carmela Migliaccio and Antonella Sardei |

It is certified that error appears in the above-identified patent and that said Letters Patent is hereby corrected as shown below:

On the Title Page

Item (56), Column 2, OTHER PUBLICATIONS: In the last reference, KHAN, p.H2135-45 should read pg. H2136-45.

Signed and Sealed this
Twenty-first Day of July, 2020

Andrei Iancu
*Director of the United States Patent and Trademark Office*